United States Patent [19]

Handel et al.

[11] Patent Number: 5,387,422
[45] Date of Patent: Feb. 7, 1995

[54] PROTEOLYTIC FUNGAL ENZYME FOOD SUPPLEMENT COMPOSITION

[75] Inventors: Richard A. Handel, Ridgewood; Rodger R. Rohde, Jr., Wayne, both of N.J.

[73] Assignee: Triarco Industries, Inc., Paterson, N.J.

[21] Appl. No.: 30,596

[22] Filed: Mar. 11, 1993

[51] Int. Cl.$^6$ .............................. A23L 1/28
[52] U.S. Cl. ..................... 426/2; 424/94.2; 424/439; 426/442; 426/648
[58] Field of Search ............ 426/2, 648, 442; 424/94.2, 439

[56] References Cited

U.S. PATENT DOCUMENTS 5,057,321  10/1991  Edgren et al. ............... 424/439

FOREIGN PATENT DOCUMENTS 2921213  12/1980  Germany .................. 426/2

OTHER PUBLICATIONS

Amano Pharmaceutical Co., Ltd., Technical Bulletin No. PEZ-1, 1977, "Prozyme 'Amano' (Proteolytic Enzyme Preparation)".
Amano Pharmaceutical Co., Ltd., Technical Bulletin No. PEZ-2, 1977, "Newlase 'Amano' (Acid--Proteolytic Enzyme Preparation)".
Foods Chemicals Codex, National Academy Press, 3rd Ed., 1981, pp. 479–481, 496–498.
Bio-Cat, Inc., "Acid Stable Protease" product brochure.
Bio-Cat, Inc., "Fungal Protease-BC", product brochure.

*Primary Examiner*—John J. Gallagher
*Attorney, Agent, or Firm*—Nicholas N. Kallas

[57] ABSTRACT

This invention relates to a proteolytic fungal enzyme food supplement composition comprising a unique combination of at least one acid protease fungal enzyme and at least one semi-alkaline protease fungal enzyme. More particularly, the invention relates to a proteolytic fungal food supplement composition comprising a unique combination of an acid protease fungal enzyme obtained from *Rhizopus niveus* or *Aspergillus niger var. macrosporus* and a semi-alkaline protease fungal enzyme obtained from *Aspergillus oryzae* or any species of Rhizopus including *Rhizopus niveus* and *Rhizopus oryzae*, wherein the acid protease fungal enzyme is present in an amount of at least 50 SAP and the semi-alkaline protease fungal enzyme is present in an amount of at least 25,000 HUT, the amounts being per gram of composition.

8 Claims, No Drawings

PROTEOLYTIC FUNGAL ENZYME FOOD SUPPLEMENT COMPOSITION

FIELD OF THE INVENTION

This invention relates to a proteolytic fungal enzyme food supplement composition comprising a unique combination of at least one acid protease fungal enzyme and at least one semi-alkaline protease fungal enzyme. More particularly, the invention relates to a proteolytic fungal food supplement composition comprising a unique combination of an acid protease fungal enzyme obtained from *Rhizopus niveus* or *Aspergillus niger var. macrosporus* and a neutral or semi-alkaline protease fungal enzyme obtained from *Aspergillus oryzae* or any species of *Rhizopus*, wherein the acid protease fungal enzyme is present in an amount of at least 50 SAP and the semi-alkaline protease fungal enzyme is present in an amount of at least 25,000 HUT, the amounts being per gram of composition.

BACKGROUND OF THE INVENTION

The subject proteolytic fungal enzyme food supplement composition was invented to meet the needs of strength athletes. These athletes were, and still are, relying upon various protein-containing foods and protein-containing food supplements in order to provide an ample supply of amino acid building blocks necessary for human muscle protein synthesis.

Many of the popular food supplements commercially available today do not contain whole food proteins, instead they contain enzymatic protein hydrolysates and/or amino acids in their free form. These food supplements, which the compositions of the present invention are intended to replace, are not only expensive, but they are usually unpalatable.

The seminal concept of the present inventive compositions is to utilize the human stomach and small intestine of the human athlete as a reaction vessel in which an ingested dietary protein will be converted into amino acids in advance of, and adjunctive to, the normal endogenous enzyme systems.

Although other digestive enzyme preparations are presently commercially available, these enzyme preparations have several limitations when used for this purpose. For example, most proteolytic preparations currently marketed use either the fruit proteases papain and/or bromelain, or the animal-derived proteases pepsin and/or pancreatin. Of these, three of the enzymes—papain, bromelain and pepsin—are useless in the neutral to alkaline environment of the small intestine, and the fourth enzyme, pancreatin, has no activity in the human stomach. In fact, pancreatin enzymes are frequently enteric-coated to prevent their hydrolytic decomposition by gastric juices. Finally, these is reticence among vegetarians and other health devotees, many of whom are also body culturists, to use animal-derived products, including the enzymes pepsin and pancreatin.

The proteolytic fungal enzyme food supplement composition of the present invention was designed for use as a tablet, capsule, powder or liquid food supplement, to be taken with protein-containing foods in order to convert ingested dietary proteins into free amino acids, which then can be used by the body for muscle protein synthesis during anabolic cycles.

The present compositions are of value to muscle builders, weight lifters, and strength athletes, as well as to those on weight-gain programs.

To the best of the inventors' knowledge, only the presently claimed proteolytic fungal enzyme food supplement composition provides a combination of highly pH- and temperature-stable proteases that are active in the pH range of the entire digestive tract, which ranges from an acidic pH of 2 in the stomach to a semi-alkaline pH of 8 in the small intestine. In addition, the present fungal protease enzymes were chosen not only for their stability and activity, but also because they rapidly produce amino acids in free form, in contrast to the enzymes papain, bromelain and pepsin which produce short chain peptides from protein substrates. This was confirmed by tests which showed that the presently claimed proteolytic enzyme food supplement composition produced over 40 percent more amino acids in free form than the enzymes pepsin and pancreatin in comparative tests conducted in a gastrointestinal simulator.

The major advantage of the present invention is that the unique combination of proteolytic fungal enzymes is able to effectively convert, in the gastrointestinal system of a human being, ingested dietary protein into free amino acids and short chain peptides, such that the proteolytic enzymatic activity continually occurs throughout the gastrointestinal pH spectrum associated with a human digestive system, thereby making readily available to the human system an enhanced amount of amino acids in the free form.

These and additional objects and advantages of the present invention are shown from the description below.

SUMMARY OF THE INVENTION

This invention relates to an enzyme food supplement composition comprising at least one acid protease fungal enzyme and at least one semi-alkaline protease fungal enzyme. This invention further relates to an enzyme food supplement composition comprising at least one acid protease fungal enzyme obtained from *Rhizopus niveus* or *Aspergillus niger var. macrosporus* and at least one semi-alkaline protease fungal enzyme obtained from *Aspergillus oryzae* or any species of *Rhizopus* including *Rhizopus niveus* and *Rhizopus oryzae*.

This invention still further relates to an enzyme food supplement composition wherein the acid protease fungal enzyme is present in an amount of at least 50 SAP per gram of composition, and the semi-alkaline protease fungal enzyme is present in an amount of at least 25,000 HUT per gram of composition.

In a further embodiment of the present invention, the enzyme food supplement composition further comprises a carrier material, such as a maltodextrin.

In a still further embodiment, the present invention relates to an enzyme food supplement composition consisting essentially of an acid protease fungal enzyme obtained from *Rhizopus niveus* or *Aspergillus niger var. macrosporus* and a semi-alkaline protease fungal enzyme obtained from *Aspergillus oryzae* or any species of *Rhizopus* including *Rhizopus niveus* and *Rhizopus oryzae*, wherein the acid protease fungal enzyme is present in an amount of at least 50 SAP and the semi-alkaline protease fungal enzyme is present in an amount of at least 25,000 HUT, the amounts being per gram of composition.

Finally, in a method of use embodiment, the present invention relates to a method of using an enzyme food supplement composition to convert, in the gastrointestinal system of a human being, ingested dietary protein into free amino acids and short chain peptides, wherein the improvement comprises using as the proteolytic fungal enzyme food supplement composition a unique combination of at least one acid protease fungal enzyme and at least one semi-alkaline protease fungal enzyme such that enzymatic activity occurs throughout the gastrointestinal pH spectrum associated with a human digestive system.

DETAILED DESCRIPTION OF THE INVENTION

The proteolytic enzyme food supplement composition in accordance with this invention includes at least one acid protease fungal enzyme and at least one semi-alkaline protease fungal enzyme. Both of these protease fungal enzymes are essential ingredients of the food supplement compositions of the present invention. Moreover, the inventors have found that the use of proteases from fungal sources provides optimum results, and therefore the source of the acid protease and semi-alkaline protease enzymes used, in accordance with this invention, is critical.

An acid protease fungal enzyme is defined as an enzyme, which is derived from a fungal source and is capable of breaking down proteins and their degradation products, polypeptides and peptides, by hydrolysis, and is active in a pH environment ranging from a pH 2 to a pH of 8, with the optimum pH being around 6.

The acid protease fungal enzymes that can be utilized include those obtained from *Rhizopus niveus* and *Aspergillus niger var. macrosporus*. Although these enzymes can be obtained by culturing the organism, then extracting and purifying the enzyme by known and conventional techniques, the inventors have found it much more efficient to purchase the acid protease fungal enzymes from any one of the following sources: Bio-Cat, Inc., Industrial Drive, Louisa, Va. 23093; Amano International Enzyme Company, Inc., 250 East Zion Crossroads, Troy, Va. 22974.

A semi-alkaline protease fungal enzyme, which is often also referred to as a neutral protease fungal enzyme, is defined as an enzyme, which is derived from a fungal source and is capable of breaking down proteins and their degradation products, polypeptides and peptides, by hydrolysis, and is active in a environment ranging from a pH of 6.0 to a pH of 11, with the optimum pH being around 8.0. Below a pH of 6.0, these semi-alkaline or neutral protease fungal enzymes are usually inactive.

The semi-alkaline or neutral protease fungal enzymes that can be utilized include those obtained from *Aspergillus oryzae* or any species of *Rhizopus* including *Rhizopus niveus* and *Rhizopus oryzae*. Although these enzymes can be obtained by culturing the organism, then extracting and purifying the enzyme by known and conventional techniques, the inventors have found it more efficient simply to purchase the semi-alkaline or neutral protease fungal enzymes from the same sources mentioned above.

The acid protease fungal enzymes and the semi-alkaline or neutral protease fungal enzymes may be used, in accordance with the subject invention, in the following concentrations: for the acid protease fungal enzyme, at least 50 SAP per gram of composition; for the semi-alkaline or neutral protease fungal enzyme, at least 25,000 HUT per gram of composition. The amount of enzyme is not critical. However, for reasons of economics, an excessive quantity of enzyme should be avoided, and for reasons of utility, at least the minimum amount to produce satisfactory results should be used.

A third ingredient which is commonly added, although not essential, to the enzyme food supplement composition is a carrier material. Suitable carrier materials include maltodextrins, modified starches, direct compression tablet excipients such as dicalcium phosphate, calcium sulfate and sucrose. A particularly preferred carrier ingredient is the 10 DE Maltrin M100 maltrodextrin from Grain Processing Corporation. Carriers can be added in concentrations ranging from 50 to 95 weight percent of the total composition.

Various other additives which are conventionally added to enzyme food supplement compositions, such as preservatives and the like, may be utilized.

One method of ingredient incorporation for the proteolytic fungal enzyme food supplement compositions, in accordance with this invention, and as used to formulate the example is as follows:

EXAMPLE

A typical proteolytic fungal enzyme food supplement composition that the inventors have formulated consists of: (1) 6.122 weight percent of acid protease (ex *Rhizopus niveus*) containing 2,000 SAP per gram of acid protease enzyme and obtained from Bio-Cat. Inc, (2) 10,000 weight percent of semi-alkaline or neutral protease (ex *Aspergillus oryzae*) containing 500,000 HUT per gram of semi-alkaline or neutral protease enzyme, also obtained from Bio-Cat, Inc., and (3) 83.878 weight percent maltodextrin, a 10 DE product sold by Grain Processing Corporation under the trade name Maltrin M100. The weight percents are weight percentages of the total composition. The 2,000 SAP per gram of enzyme for the acid protease and the 500,000 HUT per gram of enzyme for the semi-alkaline protease are standard units of proteolytic (protease) activity.

A SAP unit (Spectrophotometric Acid Protease Unit) is defined as that proteolytic activity that will liberate one micromole of tyrosine per minute under the conditions of the assay stated in the *Food Chemicals Codex*, Third Edition, *General Tests and Apparatus, Proteolytic Activity, Fungal (SAP)*, pp. 497–498. A HUT unit (Hemoglobin Unit, Tyrosine Basis) of proteolytic activity is defined as that amount of enzyme that produces, in one minute under the conditions of assay stated in the above referenced text at pages 496–497, a hemoglobin hydrolysate whose absorbance at 275 nm is the same as that of a solution containing 1.10 micrograms per milliliter of tyrosine in 0,006N hydrochloric acid.

In order to make a proteolytic fungal enzyme food supplement composition in accordance with this invention, the purified enzymes, which were purchased from Bio-Cat, Inc., were dry-blended with maltodextrin until a uniform mixture was obtained.

The present enzyme food supplement composition is ingested in the same manner as any food product and preferably taken immediately after or during ingestion of dietary protein.

Tests have demonstrated that as little as 250 milligrams of the claimed proteolytic fungal enzyme food supplement composition was able to convert the majority of protein in a one pound sirloin steak to free amino acids in a simulated human model, even without the aid of gastrointestinal enzymes.

The compositions of the present invention may be illustrated by way of the above example which is presented for illustration and not intended to be limiting to the scope of the invention. The invention is not to be limited except as set forth in the following claims.

What is claimed is:

1. A method of using an enzyme food supplement composition to convert, in the gastrointestinal system of a human being, ingested dietary protein into free amino acids and short chain peptides, wherein the improvement comprises using a combination of at least one acid protease fungal enzyme and at least one semi-alkaline protease fungal enzyme such that enzymatic activity occurs throughout the gastrointestinal pH spectrum associated with a human digestive system.

2. The method of claim 1 wherein the source of the acid protease fungal enzyme is selected from the group consisting of *Rhizopus niveus* and *Aspergillus niger var. macrosporus*.

3. The method of claim 1 wherein the source of the semi-alkaline protease fungal enzyme is selected from the group consisting of *Aspergillus oryzae* and any species of Rhizopus.

4. The method of claim 1 wherein the source of the semi-alkaline protease enzyme is selected from the group consisting of *Rhizopus niveus* and *Rhizopus oryzae*.

5. The method of claim 1 wherein the acid protease fungal enzyme is present in an amount of at least 50 SAP per gram of composition.

6. The method of claim 1 wherein the semi-alkaline protease fungal enzyme is present in an amount of at least 25,000 HUT per gram of composition.

7. The method of claim 1 further comprising a carrier material.

8. The method of claim 7 wherein the carrier material is a maltodextrin.

* * * * *